(12) United States Patent
Klein

(10) Patent No.: US 10,127,347 B2
(45) Date of Patent: Nov. 13, 2018

(54) DETERMINATION OF THE POSITION OF THE CONDYLAR ARTICULATION AXIS FOR CREATING A VIRTUAL ARTICULATOR

(71) Applicant: Sirona Dental Systems GmbH, Bensheim (DE)

(72) Inventor: Konrad Klein, Heidelberg (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 14/907,055

(22) PCT Filed: Jul. 24, 2013

(86) PCT No.: PCT/EP2013/065641
§ 371 (c)(1),
(2) Date: Jan. 22, 2016

(87) PCT Pub. No.: WO2015/010733
PCT Pub. Date: Jan. 29, 2015

(65) Prior Publication Data
US 2016/0162631 A1    Jun. 9, 2016

(51) Int. Cl.
*G06K 9/00* (2006.01)
*G06F 19/12* (2011.01)
(Continued)

(52) U.S. Cl.
CPC ............ *G06F 19/12* (2013.01); *A61C 9/0046* (2013.01); *A61C 19/045* (2013.01); *G06T 19/20* (2013.01)

(58) Field of Classification Search
CPC ..... A61C 19/045; A61C 9/0046; G06F 19/12; G06T 19/20
See application file for complete search history.

(56) References Cited

U.S. PATENT DOCUMENTS 5,440,393 A    8/1995  Wenz
8,366,442 B2*  2/2013  Schmitt ............. A61C 13/0004
                                                378/170
(Continued)

FOREIGN PATENT DOCUMENTS

EP    2 229 913 A1   9/2010
JP    06-503723 A    4/1994
(Continued)

OTHER PUBLICATIONS

P.J. Besl: "Active Optical Range Imaging Sensors", Machine Vision and Applications, 1:127-152, 1988.
(Continued)

*Primary Examiner* — Tom Y Lu
(74) *Attorney, Agent, or Firm* — Fitzpatrick, Cella, Harper & Scinto

(57) ABSTRACT

A method is proposed for creating a virtual articulator for a jaw and the associated dentition having the following steps: image a virtual model of the teeth of the maxilla (140); image a virtual model of the teeth of the mandible (130); buccal imaging of the position and orientation of the teeth (130, 140) of the maxilla and mandible in the closed-bite position; buccal imaging of the position and orientation of the teeth (130, 140) of the maxilla and mandible in a slightly open position; computational determination of the position of the condylar articulation axis (150) relative to the teeth (130, 140) of the mandible and/or maxilla from the imaged positions and orientations; and a virtual articulator can thereby be created without having to possess special knowledge, e.g. of the dimensions of a specific mechanical articulator or any adapter elements, or their arrangement.

24 Claims, 1 Drawing Sheet

(51) Int. Cl.
*A61C 19/045* (2006.01)
*A61C 9/00* (2006.01)
*G06T 19/20* (2011.01)

(56) References Cited

U.S. PATENT DOCUMENTS

| | | | |
|---|---|---|---|
| 9,084,653 B2 | 7/2015 | Jordan et al. | |
| 9,949,628 B2* | 4/2018 | Fisker | A61C 9/0046 |
| 2004/0172150 A1 | 9/2004 | Perot et al. | |
| 2008/0182220 A1* | 7/2008 | Chishti | A61C 7/00 433/24 |
| 2010/0240001 A1 | 9/2010 | Steger | |
| 2013/0054190 A1* | 2/2013 | Kadobayashi | A61C 11/00 702/155 |
| 2013/0066598 A1* | 3/2013 | Fisker | A61C 11/00 703/1 |
| 2013/0204600 A1* | 8/2013 | Mehra | G16H 50/50 703/11 |
| 2013/0325431 A1* | 12/2013 | See | A61C 7/002 703/11 |
| 2014/0370465 A1* | 12/2014 | Lucas | A61C 7/36 433/214 |

FOREIGN PATENT DOCUMENTS

| | | |
|---|---|---|
| JP | 2784690 B2 | 8/1998 |
| JP | 2001-517480 A | 10/2001 |

OTHER PUBLICATIONS

Francois Blais: "Review of 20 years of range sensor development". Journal of Electronic Imaging, 13(1): 231-240, Jan. 2004.
P.J. Besl & N.D. McKay: "A Method for Registration of 3-D Shapes". IEEE Transaction on Pattern Analysis and Machine Intelligence, vol. 14, No. 2, Feb. 1992.
Bisler et al., "The Virtual Articulator" Intl. J. of Computerized Dentistry, 2002, v. 5, pp. 101-106.
Written Opinion of the International Search Authority in PCT/EP2013/065641, dated Jan. 24, 2016.
Mizokami, Takao, et al., "Study on the Axis of small Opening and Closing Movement of the Mandible in and around Intercuspal Position", The Journal of Japan Prosthodontic Society, Japan, 1979, vol. No. 23, Issue No. 3, p. 552-560.
Office Action dated Jun. 6, 2017, in Japanese Patent Application No. 2016-528365.
English translation of Office Action dated Apr. 3, 2018, in Japanese Patent Application No. 2016-528365.

* cited by examiner

DETERMINATION OF THE POSITION OF THE CONDYLAR ARTICULATION AXIS FOR CREATING A VIRTUAL ARTICULATOR

FIELD OF THE INVENTION

The invention relates to a method and a device for the determination of the jaw geometry for the preparation of a computer-assisted, i.e., virtual, articulator. Models of dentition as well as articulators are used in the creation of the restorations. If these dental restorations are generated with the assistance of a computer (so-called "dental CAD/CAM") which, for example, is necessary with restorations made of ceramic, a computer-assisted model is required.

PRIOR ART

The document EP 2 229 913 A1 describes a device and a method for creating a computer-processable image of a dental model using a scanner and an electronic storage unit. An associated disadvantage is that the possibility of moving the jaw is not taken into account, and in particular, the condylar articulation axis is not recorded and is not available in the computer-assisted model. Consequently, grinding, chewing and biting movements cannot be simulated.

The procedure is also known of providing only the data of a specific known mechanical articulator in the virtual model. Adapter elements (for example made of plaster) by means of which the actual maxillary and mandibular models are adapted to the mechanical articulator must be additionally measured before the maxillary and mandibular models can be used in the virtual articulator since the virtual articulator is predefined just like the mechanical articulator. Among other things, it is disadvantageous in this context that the measurement of different components (models of the maxilla and mandible, adapters for the maxilla and mandible) and their orientation relative to each other leads to significant imprecision in the virtual model.

In this process, the transfer of the mechanical articulator dimensions to the digitized geometry occurs in several steps:
1. Measurement of the orientation of the adapter geometries to which the maxillary and mandibular models are adapted in the mechanical articulator relative to each other and to the condylar articulation axis of the mechanical articulator.
2. Measurement of the orientation of the articulator-equivalent adapter geometry mounted in the 3-D detection system relative to the 3-D detection system.
3. Imaging of the maxillary and mandibular model that was affixed in the 3-D detection system to the articulator-equivalent adapter geometry.

These two measuring procedures directly yield the position of the maxillary and mandibular model relative to the articulator geometry, and accordingly also to the condylar articulation axis. The two measuring procedures must be performed once for each mechanical articulator. This method has the disadvantage of error accumulation over the above-described processing chain:
  The measurement of the mechanical articulator is involved and can only be performed by the user with limited precision.
  The use of nominal dimensions incorporates production tolerances, i.e., deviations from the nominal dimensions of the specific specimen, into the processing chain.
In any case, an error-prone, data-dependent computational correction of the adjustment of the incisal pin in the articulator is needed since this generally does not produce the assumed geometry with sufficient precision. This is critical, because the relatively small contact area between the maxilla and mandible (contact points) must be used for the correction. The influence of the errors in the contact areas cannot be restricted, or can only be slightly restricted, by averaging or outlier analysis.
The measurement of the adapter geometry in the 3-D detection system is error prone.

Problem

The problem of the invention is to present a method and a device which improves the prior art computer-assisted modeling of dentition.

Solution

This problem is solved by the inventions having the features of the independent claims. Advantageous developments of the inventions are characterized in the dependent claims. The wording of all the claims is hereby included in the content of this description by way of reference.

Individual method steps will be described in greater detail in the following. The steps do not necessarily have to be performed in the indicated sequence, and the method to be described can also have additional steps which are not mentioned.

To solve the problem, a method is proposed for determining the position of the condylar articulation axis of a jaw of a mammal, such as that of a human, relative to the mandible and/or maxilla which comprises the following steps:
  buccal imaging of the position and orientation of the teeth of the maxilla and mandible in the closed-bite position;
  buccal imaging of the position and orientation of the teeth of the maxilla and mandible in a position in which the mandible or maxilla is rotated relative to the closed-bite position by an angle of 1-20°, preferably 5-10°, about the condylar articulation axis; and
  computational determination of the position of the condylar articulation axis relative to the teeth of the mandible and/or maxilla from the imaged positions and orientations.

This makes it possible to specifically determine the position of the condylar articulation axis adapted to the individual situation without having to possess special knowledge, e.g. of the dimensions of a specific mechanical articulator or any adapter elements, or their arrangement. The buccal images can either be performed directly on the patient or for example on a real model that was adjusted in a mechanical articulator. In principle, all tactile or optical measuring techniques, or possibly x-ray or ultrasound techniques, can be used as the imaging techniques.

Furthermore, a method for creating a virtual articulator for a jaw and the associated dentition is proposed to solve the problem and has the following steps:
  image a virtual model of the teeth of the maxilla;
  image a virtual model of the teeth of the mandible;
  determine the position of the condylar articulation axis of the jaw as described above relative to the teeth of the virtual model of the mandible and/or maxilla; and
  create a virtual articulator from the virtual models of the mandible and maxilla, their relative positions to each other, and the relative position of the condylar articulation axis.

Such a virtual articulator significantly improves the production of high-quality dental restorations, for example with ceramic elements, since they are only produced with the assistance of computer as it is. A virtual articulator which takes into account the condylar articulation axis also makes it possible to simulate mastication and biting movements in this context, which makes it significantly easier to specifically shape and adapt the dental restoration to be produced.

The errors mentioned in the description of the prior art are avoided in the method according to the invention. Buccal registration as a residual source of errors has a comparatively minor influence since the distance between the involved surface measurements is extensively minimized. In addition, individual measuring errors can be computationally identified, and their influence can be restricted. The position between the maxilla and mandible is determined with the same precision as the multi-image integration within the maxilla and mandible.

In principle, all tactile and/or optical measuring techniques can be used as the measuring method for recording the virtual models of the teeth. Surface measuring systems of optical metrology as summarized by Besl [1] and Blais [2] are advantageously used. In this context, the recording of a virtual model always means that images are created by the existing measuring method, and a computer calculates a virtual model from this data. If automatic controlling of the imaging device is possible, for example with a robot arm, the method can be executed in an entirely automated manner controlled by the computer.

In one advantageous development of the cited method, the position and orientation of the teeth of the maxilla and mandible, and/or the virtual model of the teeth of the maxilla and mandible, are imaged by means of surface triangulation. This method is particularly advantageous since it is harmless to health, precise and easy to perform.

Furthermore, the problem is solved with a device for determining the position of the condylar articulation axis of a jaw relative to the teeth of the mandible and/or maxilla with:
  imaging means for the buccal imaging of the position and orientation of the teeth of the maxilla and mandible;
  means for the computational determination of the position of the condylar articulation axis relative to the teeth of the mandible from
  a buccal image, taken using the imaging means, of the position and orientation of the teeth of the maxilla and mandible in the closed-bite position; and from
  a buccal image, taken using the imaging means, of the position and orientation of the teeth of the maxilla and mandible in a position in which the mandible or maxilla is rotated relative to the closed-bite position by an angle of 1-20° about the condylar articulation axis, i.e., slightly open, wherein an angle of 5-10° is preferred.

An advantageous development of the invention also provides a device for creating a virtual articulator for a jaw and the associated dentition, having:
  means for the three-dimensional imaging of the teeth of the maxilla and mandible;
  means for calculating a virtual model of the teeth of the maxilla and mandible proceeding from the three-dimensional images of the teeth of the maxilla and mandible;
  means as described above for determining the position of the condylar articulation axis of the jaw relative to the teeth of the virtual model of the mandible and/or maxilla; and
  means for calculating the virtual articulator from the virtual models of the mandible and maxilla, their relative positions to each other, and the relative position of the condylar articulation axis.

The means for the three-dimensional imaging of the teeth of the maxilla and mandible, and the imaging means which serve to determine the position of the condylar articulation axis, can be the same.

Additional details and features are found in the following description of preferred exemplary embodiments in conjunction with the dependent claims. The respective features can be implemented by themselves or severally in combination with each other. The possibilities of solving the problem are not restricted to the exemplary embodiments. For example, the ranges always comprise all uncited intermediate values and all conceivable partial intervals.

An exemplary embodiment is schematically portrayed in the FIGURE. In particular:

Figures 1A, 1B:
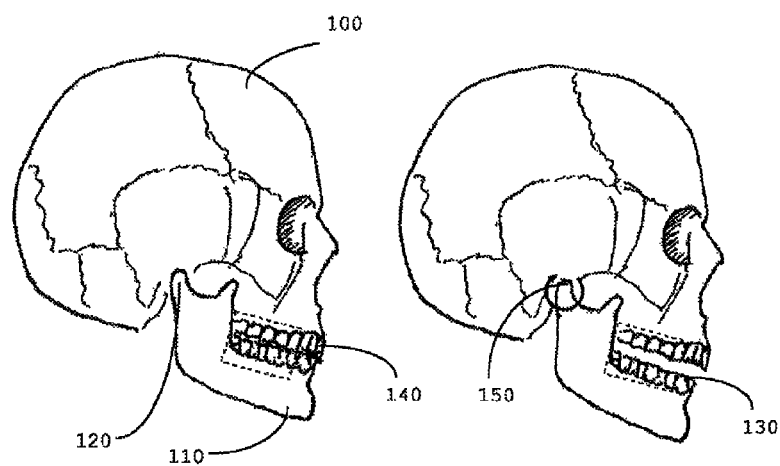
FIG. 1A shows a side view of a human skull in closed-bite position.
FIG. 1B shows a side view of a human skull with a slightly open jaw.

In a preferred embodiment of the method according to the invention, virtual models of the teeth of the maxilla and mandible are first recorded. An optical 3-D measuring system is used which images these models using surface triangulation with the assistance of structured illumination. A computer calculates virtual models from these images. Then at least two buccal images are made using the same imaging method. FIGS. 1A and 1B show side views of the skull 100 in these images. The mandible 110 is connected by means of the condyles (joint heads) 120 via the temporomandibular joint to the rest of the skull and can rotate on this joint (oversimplified). However, the precise shape of the maxilla and mandible does not play a role in this consideration; at issue in particular is the modeling of the dentition, i.e., the position and orientation of the teeth 130 of the mandible and the teeth 140 of the maxilla.

First, a buccal image is made in closed-bite position as depicted in the left half of the FIGURE. Subsequently, another buccal image is made with the jaw slightly open, wherein the opening is achieved by rotating the mandible on the condylar articulation axis 150 by an angle of typically 5-10°. This is shown in the right half of the FIGURE. The imaged data are recorded using the method of Besl and McKay [3]. From the registered data, the computer calculates the position of the condylar articulation axis in the virtual model, wherein a virtual articulator is available that does not depend on the data of any predetermined articulator, but rather precisely fits the dentition to be processed. The calculation is preferably based on a quaternion approach. The recalculation of the rotation matrix known from the registration into a quaternion can in principle be derived from an eigenvector problem; preferably, however, an algorithm is used with numerous definitions by cases http://www.cg.info.hiroshima-cu.ac.jp/~miyazaki/knowledge/teche52.html and Q55 in http://www.cs.princeton.edu/~gewang/projects/darth/stuff/quat_faq.html). The translatory component of the relative orientation is mapped in the process onto a shift along the rotational axis.

Numerous alterations and developments of the described exemplary embodiments are realizable. For example, very different (3-D) measuring and imaging methods can accordingly be used.

Furthermore, different registration methods familiar to a person skilled in the art can be used. In addition, the registration can be carried out differently, for example:

determination of the condylar articulation axis from two buccal images which are registered in sections together, or determination of the condylar articulation axis from two buccal images which are registered in sections with the maxillary and mandibular data.

Furthermore, the features of the virtual articulator can be altered in many ways with respect to the desired use without having thereby altered the essence of the invention.

Glossary

Articulator

Device for simulating the movement of the temporomandibular joint. To accomplish this, plaster models of the dental arch of the maxilla and mandible are mounted in occlusion in the articulator. Then the movement of the jaws relative to each other can be simulated, which is essential to the production of dental restorations, partial or total prostheses, or retainers. (Source: http://de.wikipedia.org/wiki/Artikulator)

Buccal:

Cheek side (lat. "bucca", cheek).

Dentition

Dentition designates the entirety of the teeth of a vertebrate. This is where the chain of digestion begins: The dental arches in the maxilla and mandible (incisors, canines and molars) compress, tear apart and break down food. (Source: http://de.wikipedia.org/wiki/Gebiss)

Jaw

The jaw is the part of the facial skull which is used for consuming food by most vertebrates and therefore usually has teeth. It consists of the upper jaw (lat. maxilla) and the lower jaw (lat. mandibula). The teeth are anchored in the tooth sockets (dental alveoli) by a gomphosis (dental alveolar joint). In mammals, the mandible is movably attached at the temporomandibular joint to the temporal bone. The maxilla and mandible are therefore only indirectly connected to each other. The maxilla is immovable in mammals; in mammals, only the mandible is moved by the masticatory musculature.

(Source: http://de.wikipedia.org/wiki/Kiefer_(Anatomie))

Condylar Articulation Axis of the Temporomandibular Joint

The mandibular bone consists of the horseshoe-shaped mandibular body (corpus mandibulae), from which the ascending branch proceeds on both sides (ramus mandibulae). Two additional appendages extend from the ascending branch: The mandibular condylar process (or mandibular articular process) with its roller-shaped joint head (caput mandibulae or condyle) forms the movable part of the temporomandibular joint. The axis running through the two joint heads (condyles) is designated the condylar articulation axis. When opening and closing, the mandible rotates relative to the rest of the skull on the axis, providing that the angle remains small.

Closed-Bite Position

The closed-bite position designates maximum intercuspidation (in Latin cuspis=point). This is the position of the mandible in which there is maximum multipoint contact between the mandibular and maxillary teeth.

Triangulation

A geometric method of optically measuring distance by precisely measuring the angles within triangles. If the beam direction and distance between a camera and a light source are known, the distance from the surface points of an object to the camera can be determined. The lines between the camera and light source and the two beams from and to the object form a triangle. The three-dimensional detection (measurement) of the entire surface of an object can be realized using this method. In the triangulation of surfaces, the object to be measured is illuminated successively by the light source with patterns of strips of different widths. The surface of the object can be reconstructed therefrom by computation. More information can be found at http://www.uni-stuttgart.de/ito/forschung/forschung_3d/Streifen-projektion/ and http://www.uni-stuttgart.de/ito/forschung/forschung_3d/DSFP/.

CITED LITERATURE

Cited Patent Literature

EP 2 229 913 A1

Cited Non-Patent Literature

[1] P. J. Besl: "Active Optical Range Imaging Sensors". In J. L. C. Sanz (editor): "Advances in Machine Vision", p. 1-63. Springer-Verlag, New York, 1989.
[2] Francois Blais: "Review of 20 years of range sensor development". Journal of Electronic Imaging, 13(1): 231-240, January 2004.
[3] P. J. Besl & N. D. McKay: "A Method for Registration of 3-D Shapes". IEEE Transaction on Pattern Analysis and Machine Intelligence, Vol. 14, No. 2, February 1992. http://www.cg.info.hiroshima-cu.ac.jp/~miyazaki/knowledge/teche52.html, last accessed on Jul. 2, 2013
Q55 in
http://www.cs.princeton.edu/~gewang/projects/darth/stuff/quat_faq.html, last accessed on Jul. 2, 2013

The invention claimed is:

1. A method for determining a position of a condylar articulation axis, the method comprising:
   receiving (i) image data of a plurality of teeth located in a maxilla and a mandible when the maxilla and mandible are in a closed-bite position, and (ii) image data of the plurality of teeth when the mandible is rotated relative to the closed-bite position by an angle of 1-20° about the condylar articulation axis;
   determining:
      (i) positions and orientations of the plurality of teeth when the maxilla and mandible are in the closed-bite position based on the image data of the plurality of teeth when the maxilla and mandible are in the closed-bite position, and
      (ii) positions and orientations of the plurality of teeth when the mandible is rotated relative to the closed-bite position based on the image data of the plurality of teeth when the mandible is rotated relative to the closed-bite position; and
   determining a position of the condylar articulation axis relative to a plurality of teeth of the mandible and/or maxilla from (i) the positions and orientations of the plurality of teeth when the maxilla and mandible are in the closed-bite position, and (ii) the positions and orientations of the plurality of teeth when the mandible is rotated relative to the closed-bite position.

2. A method for creating a virtual articulator, the method comprising:
   imaging a plurality of teeth in a virtual model of a maxilla and a virtual model of a mandible to generate first image data, wherein the virtual model of the maxilla and the virtual model of the mandible are in a closed-bite position;

imaging the plurality of teeth in the virtual model of the maxilla and the virtual model of the mandible to generate second image data, wherein the virtual model of the mandible is rotated with respect to the virtual model of the maxilla about a condylar articulation axis of the jaw;

determining a position of the condylar articulation axis relative to the teeth in the virtual model of the mandible and/or the teeth in the virtual model of the maxilla based on the first image data and the second image data; and creating a virtual articulator from the virtual model of the mandible, the virtual model of the maxilla, and the determined position of the condylar articulation axis.

3. The method according to claim 1, wherein the image data of the plurality of teeth when the maxilla and mandible are in the closed-bite position and the image data of the plurality of teeth when the mandible is rotated relative to the closed-bite position are generated by surface triangulation.

4. A device for determining the position of the condylar articulation axis of a jaw, the device comprising:

an imaging unit for imaging teeth in a maxilla and a mandible; and a computer configured to:
determine a position of the condylar articulation axis relative to the teeth of the mandible and/or maxilla from (i) image data of the teeth of the maxilla and mandible in a closed-bite position generated by the imaging unit, and (ii) image data generated by the imaging unit of the teeth of the maxilla and mandible in a position in which the mandible is rotated relative to the closed-bite position by an angle of 1-20° about the condylar articulation axis.

5. A device for creating a virtual articulator for a jaw, the device comprising:

a computer configured to:
image a plurality of teeth in a virtual model of a maxilla and a virtual model of a mandible to generate first image data, wherein the virtual model of the maxilla and the virtual model of the mandible are in a closed-bite position, image the plurality of teeth in the virtual model of the maxilla and the virtual model of the mandible to generate second image data, wherein the virtual model of the mandible is rotated with respect to the virtual model of the maxilla about a condylar articulation axis of the jaw, determine a position of the condylar articulation axis relative to teeth in the virtual model of the mandible and/or the teeth in the virtual model of the maxilla based on the first image data and the second image data, and create a virtual articulator from the virtual model of the mandible, the virtual model of the maxilla, and the determined position of the condylar articulation axis.

6. The method according to claim 1, wherein the image data of the plurality of teeth when the maxilla and mandible are in the closed-bite position corresponds to a buccal image, and wherein the image data of the plurality of teeth when the mandible is rotated relative to the closed-bite position corresponds to a buccal image.

7. The method according to claim 1, wherein the determining of the position of the condylar articulation axis relative to the teeth of the mandible and/or maxilla is based on a quaternion approach.

8. The method according to claim 1, wherein the plurality of teeth are located in a patient's jaw.

9. The method according to claim 1, wherein the plurality of teeth are located in a plaster model of a patient's jaw.

10. The device according to claim 4, wherein the imaging unit is configured to perform the imaging of the teeth in the maxilla and mandible by surface triangulation.

11. The device according to claim 4, wherein the image data of the teeth of the maxilla and mandible in the closed-bite position corresponds to a buccal image, and the image data of the teeth of the maxilla and mandible in a position in which the mandible is rotated relative to the closed-bite position corresponds to a buccal image.

12. The device according to claim 4, wherein the determination of the position of the condylar articulation axis relative to the mandible and/or maxilla is based on a quaternion approach.

13. The device according to claim 4, wherein the teeth in the maxilla and mandible are located in a patient's jaw.

14. The device according to claim 4, wherein the teeth in the maxilla and mandible are located in a plaster model of a patient's jaw.

15. The method according to claim 2, further comprising:
receiving image data of a plurality of teeth in a maxilla and a mandible; and
creating the virtual model of the maxilla and the virtual model of the mandible from the received image data.

16. The method according to claim 15, wherein the received image data is optical image data generated by surface triangulation.

17. The method according to claim 2, wherein the first image data corresponds to a buccal image, and wherein the second image data corresponds to a buccal image.

18. The method according to claim 2, further comprising:
registering the first image data and the second image data, wherein the determining of the position of the condylar articulation axis is based on registered first image data and second image data.

19. The method according to claim 2, wherein the determining of the position of the condylar articulation axis is based on a quaternion approach.

20. The device according to claim 5, wherein the computer is further configured to:
receive image data of a plurality of teeth in a maxilla and a mandible, and
create the virtual model of the maxilla and the virtual model of the mandible from the received image data.

21. The device according to claim 5, wherein the received image data is optical image data generated by surface triangulation.

22. The device according to claim 5, wherein the first image data corresponds to a buccal image, and wherein the second image data corresponds to a buccal image.

23. The device according to claim 5, wherein the computer is further configured to:
register the first image data and the second image data, and
determine the position of the condylar articulation axis based on registered first image data and second image data.

24. The device according to claim 5, wherein the position of the condylar articulation axis is determined based on a quaternion approach.

\* \* \* \* \*